US012668771B2

(12) United States Patent
Bell et al.

(10) Patent No.: US 12,668,771 B2
(45) Date of Patent: Jun. 30, 2026

(54) HARVEST AND CONCENTRATION PROCESS FOR MICROALGAE SPECIES

(71) Applicant: SMARTFLOW TECHNOLOGIES, INC., Sanford, NC (US)

(72) Inventors: Jason Bell, Sanford, NC (US); Todd Benson, Sanford, NC (US); Marc Pugh, Sanford, NC (US)

(73) Assignee: SMARTFLOW TECHNOLOGIES, INC., Sanford, NC (US)

( * ) Notice: Subject to any disclaimer, the term of this patent is extended or adjusted under 35 U.S.C. 154(b) by 359 days.

(21) Appl. No.: 18/457,813

(22) Filed: Aug. 29, 2023

(65) Prior Publication Data

US 2024/0067921 A1 Feb. 29, 2024

Related U.S. Application Data

(60) Provisional application No. 63/373,922, filed on Aug. 30, 2022.

(51) Int. Cl.
*C12N 1/12* (2026.01)
*C12M 1/00* (2006.01)
*C12M 1/12* (2006.01)

(52) U.S. Cl.
CPC ............... *C12N 1/12* (2013.01); *C12M 37/02* (2013.01); *C12M 47/02* (2013.01)

(58) Field of Classification Search
CPC ............ C12N 1/12; C12N 1/02; C12M 37/02; C12M 47/02; C12M 21/02
See application file for complete search history.

(56) References Cited

U.S. PATENT DOCUMENTS

| | | | |
|---|---|---|---|
| 4,867,876 A | 9/1989 | Kopf |
| 4,882,050 A | 11/1989 | Kopf |
| 5,034,124 A | 7/1991 | Kopf |
| 5,049,268 A | 9/1991 | Kopf |
| 5,232,589 A | 8/1993 | Kopf |
| 5,342,517 A | 8/1994 | Kopf |
| 5,593,580 A | 1/1997 | Kopf |
| 5,868,930 A | 2/1999 | Kopf |
| 10,987,631 B2 | 4/2021 | Benson et al. |
| 11,654,397 B2 | 5/2023 | Benson et al. |
| 2002/0034817 A1 | 3/2002 | Henry et al. |
| 2002/0079270 A1 | 6/2002 | Borodyanski et al. |
| 2004/0121447 A1 | 6/2004 | Fournier |
| 2012/0264194 A1 | 10/2012 | Kale |
| 2013/0164824 A1 | 6/2013 | Licamele et al. |
| 2019/0330587 A1 | 10/2019 | Hazlebeck et al. |
| 2023/0302410 A1 | 9/2023 | Benson et al. |

OTHER PUBLICATIONS

International Search Report and Written Opinion for PCT/US2023/073081, mailed Jan. 3, 2024, 4pgs.

*Primary Examiner* — Lynn Y Fan
(74) *Attorney, Agent, or Firm* — Casimir Jones, S.C.; Tristan A. Fuierer

(57) ABSTRACT

An apparatus and method of separating microalgae from a liquid source material, wherein the apparatus and method permit the efficient achievement of a high concentration of microalgae in a final solid-containing fraction.

16 Claims, 5 Drawing Sheets

RETENTATE OUTLET

PERMEATE OUTLET

PERMEATE INLET (opt)

"Permeate Packs" (20/30/20)

holder plate holder plate

Exit from flow channel

Entrance to flow channel

10

RETENTATE INLET

HARVEST AND CONCENTRATION PROCESS FOR MICROALGAE SPECIES

CROSS REFERENCE TO RELATED APPLICATIONS

This application claims priority to U.S. Provisional Patent Application No. 63/373,922 filed on Aug. 30, 2022 in the name of Jason Bell et al., and entitled "Harvest and Concentration Process for Microalgae Species," which is hereby incorporated by reference herein in its entirety.

FIELD

The present invention relates an apparatus and method of separating microalgae cells from a liquid source material.

BACKGROUND

Green microalgae are microscopic single-cell plants typically found in water systems such as oceans, lakes, rivers, and streams. Algae are the first link in the oceanic food chain and use photosynthesis to convert water and carbon dioxide to nutrient-rich biomass and oxygen in the presence of sunlight. Other marine sources of Omega-3 oil such as fish and krill, do not produce Omega-3 and long chain fatty acids like Eicosapentaenoic acid (EPA) and Docosahexaenoic acid (DHA), but rather accumulate it from the algae they and their prey consume in their natural environment.

A range of microalgae species are cultivated at large scale around the world and are commercially used in a variety of applications such as aquaculture, cosmetics, and food supplements. Microalgae can not only be used for lipid and specialty fat production but also sustainable protein production for use in livestock or human food. Important for human health, algae species are the world's primary producers of oxygen and an important source for nutrients such as the Omega-3 fatty acids (e.g., EPA and DHA), proteins, antioxidants and other micronutrients. Omega-3 fatty acids have research-proven health benefits that people depend on each day for more energy, a healthy heart, brain development, inflammation reduction, and a healthy mood.

Algae cultivation farms (e.g., Photobio Reactors (PBR) or Open Raceway Ponds (ORP) such as an Oswald system) can be considered a hydroponic farm that allows for continuous harvest of the valuable component within the microalgae product including, but not limited to, omega-3 fatty acids, proteins, essential minerals, fiber, and vitamins. In comparison to traditional row crops, per acre yields at the algae cultivation farms are 10× to 300× that of row crop yield, depending on species strain and the specific row crop. Advantageously, algae cultivation farms can also be located on non-productive land and can be grown in salty water unlike traditional row crops.

It has long been recognized that algae harvesting is a major obstacle to realizing practical and economical unicellular algae production. Algae is typically harvested at very low concentrations for industrial processing typically in a range from about 0.02 wt % to about 5-6 wt %, depending on the cultivation process (i.e., ORP or PBR), so large amounts of water must be removed from algae mediums to recover algae product having a high algae concentration (e.g., greater than 6-8 wt %, preferably greater than 10 wt %, solids content). Traditionally, commercial algae harvesting facilities have used a centrifuge or a dissolved air floatation system followed by centrifugation to harvest and dewater algae. Centrifuges, however, have high capital, high operating costs and low capture efficiency, and dissolved air floatation systems typically require an addition of a coagulant or flocculent, which increases operating costs and can cause problems for production facilities that recycle their media. In addition, flocculation is not preferred when the intended product is the solid phase since the flocculants typically will have to be separated from the target solid. Electrocoagulation, cross flow filtration, bioflocculation, vibrating membrane filtration, evaporation, and ultrasonic harvesting have been proposed as alternatives to centrifuges and air flotation systems, but an algae harvesting system having low operating costs and minimal energy requirements has remained elusive. For example, some tangential flow filtration (TFF) formats such as hollow fibers have a limited concentration maximum, requiring substantial additional processing and hence driving up the costs.

A new method of concentrating and drying microalgae is needed, one that has a higher efficiency of concentration of the algae than traditional methods known in the art. The technology preferably allows for a higher efficiency of dewatering of the algae, providing multiple improvements over the prior art apparatuses and methods including, but not limited to, lower storage capacity requirements, the ability to utilize drying methods not previously considered, improved product quality, bioactivity, and bioavailability, and lower overall operational costs.

SUMMARY

In one aspect, the present invention relates to apparatus for concentrating microalgae from a liquid source material, wherein following passage through the apparatus, a concentration of microalgae in a final concentrated solid-containing fraction is at least 6-8 wt %, based on the total weight of the final concentrated solid-containing fraction, said apparatus comprising: at least one leg for separating and concentrating a liquid source material to yield the final concentrated solid-containing fraction, wherein each leg comprises:

(i) a separation unit comprising at least one separation stage, wherein each separation stage comprises an apparatus that can dewater the liquid source material to yield a first liquid fraction and a separation stage solid-containing fraction, wherein when there is more than one separation stage, they are communicatively connected (I) in series, and a separation stage solid-containing fraction is serially moved through to a next separation stage in the series for additional dewatering, or (II) in parallel, wherein separation stage solid-containing fractions from each separation stage are combined, or (III) some combination of both (I) and (II), eventually yielding a final separation solid-containing fraction; and (ii) a concentration unit comprising at least one concentration stage, wherein each concentration stage comprises an apparatus that can concentrate the final separation solid-containing fraction to yield a second liquid fraction and a concentrated solid-containing fraction, wherein when there is more than one concentration stage, they are communicatively connected (I) in series, and a concentration stage solid-containing fraction is serially moved through to a next concentration stage in the series for additional concentration, or (II) in parallel, wherein concentration stage solid-containing fractions from each concentration stage are combined, or (III) some combination of both (I) and (II), eventually yielding the final concentrated solid-containing fraction.

In another aspect, a method of obtaining microalgae from a liquid source material is described, wherein the microalgae have a concentration in a final concentrated solid-containing fraction of at least 6-8 wt %, based on the total weight of the final concentrated solid-containing fraction, wherein the method comprises introducing a liquid source material to an apparatus described herein to yield the final concentrated solid-containing fraction.

Other aspects and advantages of the invention will be more fully apparent from the ensuing disclosure and appended claims.

DETAILED DESCRIPTION

Figure 1:
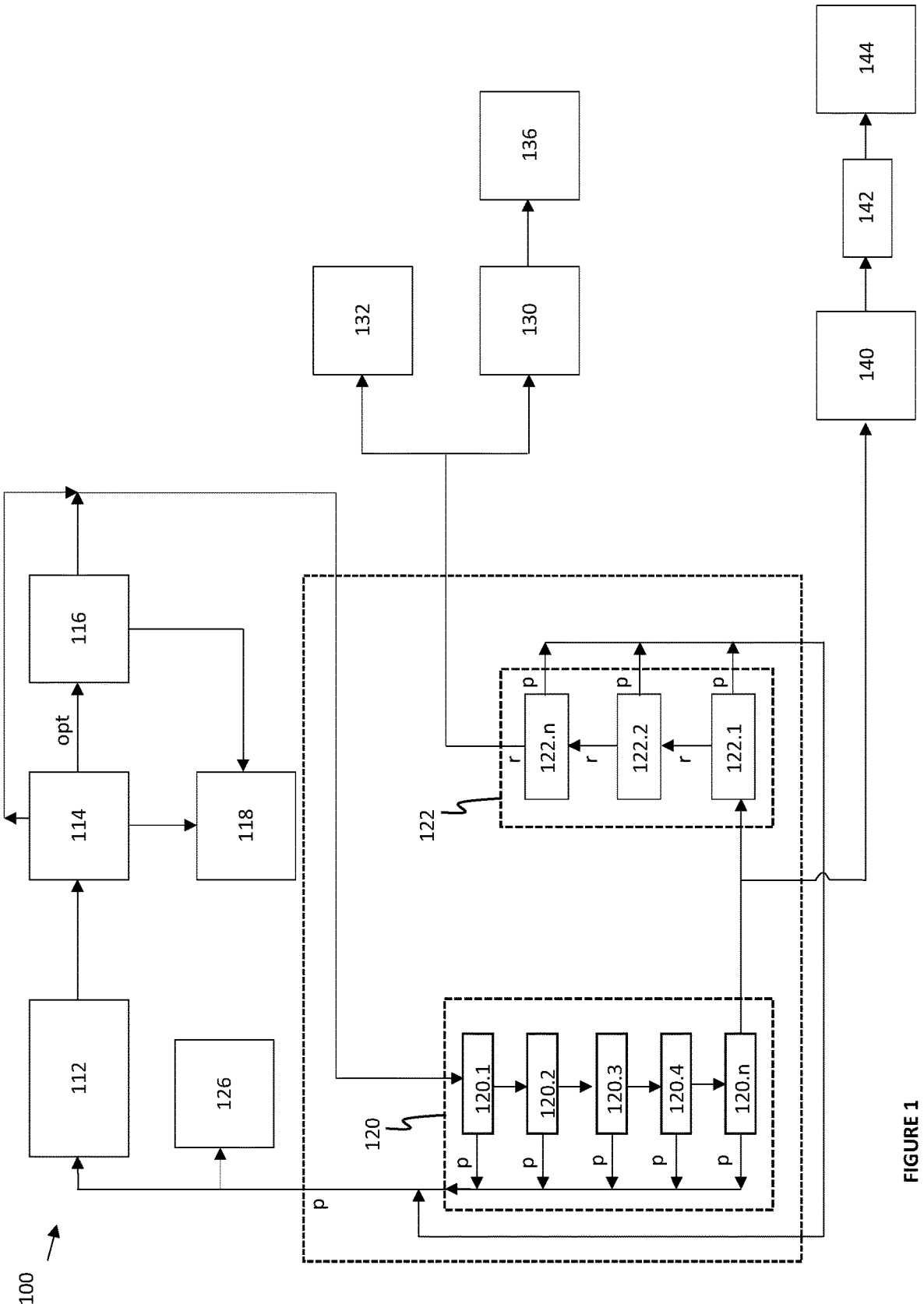
FIG. 1 illustrates a schematic of the apparatus described herein.

While not to be construed as limiting, the terms used herein have the following definitions unless indicated otherwise.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents, and other references mentioned herein are incorporated by reference in their entirety. The materials, methods, and examples disclosed herein are illustrative only and not intended to be limiting.

"About" and "approximately" are used to provide flexibility to a numerical range endpoint by providing that a given value may be "slightly above" or "slightly below" the endpoint without affecting the desired result, for example, +/−5%.

The phrase "in one embodiment" or "in some embodiments" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, a "system" refers to a plurality of real and/or abstract elements operating together for a common purpose. In some embodiments, a "system" is an integrated assemblage of hardware and/or software elements. In some embodiments, each component of the system interacts with one or more other elements and/or is related to one or more other elements. In some embodiments, a system refers to a combination of components and software for controlling and directing methods.

As defined herein, "weight percent" or "wt %" are understood to mean the dry mass of the species of interest relative to the total mass of the medium comprising said species of interest, multiplied by 100.

The term "cross-flow filtration cassette" refers to a type of filter module or filter cassette that comprises two end plates and at least one assembly of sheets positioned therebetween, wherein the at least one assembly of sheets comprises at least one porous filter element across a surface of which the liquid source material to be filtered is flowed in a tangential flow fashion, for permeation through the filter element of selected component(s) of the liquid source material. In a cross-flow filter, the shear force exerted on the filter element (separation membrane surface) by the flow of the liquid source material serves to oppose accumulation of solids on the surface of the filter element. Cross-flow filters include macrofiltration, microfiltration, ultrafiltration, and nanofiltration, and low pressure forward osmosis, or reverse osmosis membranes.

As used hereinafter, the term "sheet member" or "sheet" refers to the various laminae of the assembly of sheets, the "assembly" comprising a stack of generally planar sheet members forming an operative mass transfer unit positioned between assembly end plates. The assembly comprises assembly end plates, permeate sheets, filter sheets, retentate sheets, and optionally permeate screen spacer sheets, coupled to one another in such manner as to permit flow of the fluid to be separated through the flow channel(s) of the device, for mass transfer involving passage of the permeate through the filter sheets, and retention of the retentate on the side of the filter sheet opposite the side from which the permeate emerges.

As defined herein, a "module" or a "cassette" or a "filter cassette" or a "filter module" are intended to be synonymous and the terms interchangeable.

"Liquid source material," as used herein, refers to a liquid containing at least one and possibly two or more target substances or products of value which are sought to be separated and purified. Liquid source materials may for example be present as aqueous solutions, organic solvent systems, or aqueous/organic solvent mixtures or solutions. The liquid source material comprising the target substance can be a solid-liquid mixture or a liquid-liquid mixture. In one embodiment, the liquid source material is obtained from the at least one algae cultivator.

"Target substance" as used herein refers to the solid material to be separated from the liquid source materials. The target substance comprises one or more "target organisms" which is the microalgae to be concentrated and dried using the apparatus and methods described herein. For the purposes of the present application, target substances include, but are not limited to, at least one of viable microalgae cells, non-viable microalgae cells, rotifers, bacteria, environmental detritus, and additional organisms that may be present in the cultivation process stream. Depending on the position in the apparatus or method, the target substance can be in the liquid fraction, in the solid fraction, or both. It should also be appreciated that the target substance may be present in a permeate as well, as understood by the person skilled in the art.

As defined herein, a "permeate" is the liquid fraction that passes through the pores of a filter or permeate sheet in a filtration device, while a "retentate" is the fraction, often comprising solids, that does not pass through the pores of said filter or permeate sheet in the filtration device. The terms "supernatant" or "supernate" or "centrate" are understood to describe the liquid fraction obtained by centrifugation, while a "precipitate" or "retentate" describes the more dense, solid fraction obtained by centrifugation or the solid remaining subsequent to evaporation. Hereinafter, it is understood that a "liquid fraction" may be a permeate or a supernate and that a "solid-containing fraction" may be a retentate or a precipitate, depending on the nature of the separation or concentration.

One of the advantages of the present apparatus and method is that the liquid fraction obtained is substantially free of the target substances originally present in the liquid source materials, so that the liquid fraction can be recycled back to the ORP or PBR for reuse as cultivation media. Advantageously, the liquid fraction comprises nutrients that can be repeatedly reused, thus minimizing the amount of newly sourced nutrients necessary for the growth of new microalgae in the cultivation media. This results in a substantial savings in nutrient costs and thus a larger net profit for the grown and harvested microalgae per acre. As defined herein, "substantially free of the target substances originally present in the liquid source materials" means that the liquid fraction contains less than about 5 wt % target substances, preferably less than about 3 wt % target substances, even more preferably less than about 2 wt % target substances, and most preferably less than about 1 wt % target substances. It is understood by the person skilled in the art that the target substance comprises the target organism(s) (i.e., the microalgae), which may be separated from the other, less desirable, target substances.

As defined herein, a target substance comprising "viable microalgae cells" or "substantially viable" microalgae cells is a substance wherein a substantial amount of the microalgae cells are still alive, for example, at least 50%, at least 60%, at least 70%, at least 75%, at least 80%, at least 90%, or at least 95% of the algae cells are still alive. Advantageously, the viable microalgae cells or substantially viable microalgae cells can be used as an active inoculum for cultivation or can be prepared for continued growth/replication.

As defined herein, "microalgae" are understood to be unicellular, eukaryotic species, typically found in freshwater and marine systems, having a size in a range from about 0.5 micron to 300 microns. In one embodiment, the microalgae have a size in a range from about 1 micron to about 20 microns. The microalgae of the invention include, but are not limited to, green algae (i.e., viridiplantae), diatoms (i.e., Bacillariophyceae), dinoflagellates, and red algae (i.e., rhodophyta). Although technically not unicellular, for the purposes of the present description, spiralina (i.e., blue-green algae) is also considered microalgae. Although it is understood that the term "algae" includes "microalgae" and "macroalgae," for the purposes of this disclosure "microalgae" and "algae" are intended to be used interchangeably for simplicity. For the purposes of the present invention, the microalgae can be heterotrophic or photoautotrophic.

As defined herein, "substantially maintaining or preserving algae cell bioavailability" is defined as alive in a state of suspension, having an increased shelf life, able to reproduce/split for biomass replication/growth, and/or not damaging the algae cell using the system/apparatus and methods describe herein. By maintaining or preserving algae cell bioavailability, algae cells collected during the process may be used to innoculate incubators/bioreactors, can be stored for long periods of time without a substantial loss of any of the valuable nutrients contained therein, and can otherwise withstand the rigors of the apparatus and method while still maintaining their nutritional value.

As defined herein, "substantially maintaining or preserving algae cell bioactivity" is understood to correspond to the isolation of algae cells using a process described herein, wherein the algae cells obtained comprise a higher amount of beneficial nutrients, for example, fatty acid content, relative to algae cells grown in the same cultivator/bioreactor and isolated using a different separation process. Advantageously, the algae cells obtained using an apparatus and a process described herein are separated from the liquid source material using less harsh conditions and as such, a larger amount of valuable nutrients can be extracted from the algae cells once they are isolated, based on the total amount of isolated algae cells.

As defined herein, "some combination" is any value between greater than 0% and less than 100%.

As defined herein, a "dry" microalgae product, or one dried to "dryness," is a shelf stable material, having less than about 25% moisture, preferably less than about 20% moisture, and even more preferably less than about 12% moisture, and can be stored viably for at least one month without refrigeration.

As defined herein, "non-exogenous drying" describes a drying operation where no heat is added but the material still undergoes drying, thereby maintaining the bioavailability of lipids, proteins and carbohydrates in the material being dried. It is understood by "drying," the water is removed or otherwise driven off the product, i.e., algal cells. Oil, which is considered dry matter, may still be present in the product.

Apparatus

In a first aspect, an apparatus for separating a target material from a liquid source material is described, wherein said apparatus comprises (i) at least one concentration unit or (ii) at least one separation unit and at least one concentration unit, such that passage of the liquid source material through the apparatus yields a concentrated target organism. For the purposes of the present description, the separation unit efficiently dewaters the liquid source material when the concentration of microalgae contained therein is less than about 4 wt %. Accordingly, if the concentration of microalgae from the cultivator is greater than about 4 wt %, e.g., from a PBR, the at least one separation unit may not be needed. In one embodiment, the target organism comprises microalgae cells, for example, a *Nannochloropsis* species.

Broadly, in a first aspect, an apparatus for separating algae from a liquid source material comprising same is described, wherein the apparatus comprises (i) at least one concentration unit or (ii) at least one separation unit and at least one concentration unit, such that passage of the liquid source material through the apparatus yields a concentrated algae product. In one embodiment, passage of the liquid source material through the apparatus described herein can yield a concentrated algae product that comprises substantially viable algae cells. In another embodiment, passage of the liquid source material through the apparatus described herein can yield a concentrated algae product that comprises nonviable algae cells. In still another embodiment, the algal cells remain viable only after passage of the liquid source material through the at least one separation unit. Unexpectedly, the apparatus described herein enables the collection of a concentrated algae product that has less water than any other apparatuses or methods known in the art, specifically yielding concentrated algae products having a concentration of at least 4 wt %, preferably at least 15 wt %, even more preferably at least 20-25 wt %, and most preferably at least 30 wt %, based on the total weight of the final concentrated solid-containing fraction. The concentrated algae product can then be dried, requiring less expensive and/or previously impractical alternatives for drying because of the lower amount of water in the concentrated algae product relative to that obtained using the apparatuses of the prior art. Further, all or a portion of the liquid fraction from the apparatus can be recycled back to the ORP or PBR for reuse as cultivation media without any further treatment.

In one embodiment of the first aspect, an apparatus for concentrating microalgae from a liquid source material is described, wherein following passage through the apparatus, a concentration of microalgae in a final concentrated solid-containing fraction is at least 6-8 wt %, or at least 10 wt %, or at least 15 wt %, or at least 20 wt %, or at least 25 wt %, or at least 30 wt %, based on the total weight of the final concentrated solid-containing fraction, said apparatus comprising: at least one leg for separating and concentrating a liquid source material to yield the final concentrated solid-containing fraction, wherein each leg comprises:

(i) a separation unit comprising at least one separation stage, wherein each separation stage comprises an apparatus that can dewater the liquid source material to yield a first liquid fraction and a separation stage solid-containing fraction, wherein when there is more than one separation stage, they are communicatively connected (I) in series, and a separation stage solid-containing fraction is serially moved through to a next separation stage in the series for additional dewatering, or (II) in parallel, wherein separation stage solid-containing fractions from each separation stage are combined, or (III) some combination of both (I) and (II), eventually yielding a final separation solid-containing fraction; and (ii) a concentration unit comprising at least one concentration stage, wherein each concentration stage comprises an apparatus that can concentrate the final separation solid-containing fraction to yield a second liquid fraction and a concentrated solid-containing fraction, wherein when there is more than one concentration stage, they are communicatively connected (I) in series, and a concentration stage solid-containing fraction is serially moved through to a next concentration stage in the series for additional concentration, or (II) in parallel, wherein concentration stage solid-containing fractions from each concentration stage are combined, or (III) some combination of both (I) and (II), eventually yielding the final concentrated solid-containing fraction.

In one embodiment, prior to passage through the apparatus, the concentration of microalgae in the liquid source material is less than about 4 wt %, based on the total weight of the liquid source material. In one embodiment, the algae cell bioactivity or bioavailability is substantially maintained or preserved using the apparatus. In another embodiment, the algae cell bioactivity or bioavailability is substantially maintained or preserved only after passage through the separation unit of the apparatus.

In another embodiment of the first aspect, an apparatus for concentrating microalgae from a liquid source material is described, wherein prior to passage through the apparatus, the concentration of microalgae in the liquid source material is greater than about 4 wt %, based on the total weight of the liquid source material, and wherein following passage through the apparatus, the concentration of microalgae in a final concentrated solid-containing fraction is at least 6-8 wt %, or at least 10 wt %, or at least 15 wt %, or at least 20 wt %, or at least 25 wt %, or at least 30 wt %, based on the total weight of the final concentrated solid-containing fraction, said apparatus comprising:

at least one leg for concentrating a liquid source material to yield the final concentrated solid-containing fraction, wherein each leg comprises a concentration unit comprising at least one concentration stage, wherein each concentration stage comprises an apparatus that can concentrate the liquid source material to yield a second liquid fraction and a concentrated solid-containing fraction, wherein when there is more than one concentration stage, they are communicatively connected (I) in series, and a concentration stage solid-containing fraction is serially moved through to a next concentration stage in the series for additional concentration, or (II) in parallel, wherein concentration stage solid-containing fractions from each concentration stage are combined, or (III) some combination of both (I) and (II), eventually yielding the final concentrated solid-containing fraction.

The apparatus of any of the embodiments of the first aspect can further comprise at least one of (I) at least one incubator upstream of at least one leg, where the microalgae are cultivated, (II) at least one pre-filtration unit to remove unwanted materials from a liquid source material comprising the cultivated microalgae to yield a pre-filtered liquid source material, (III) at least one invasive pest filtration unit to remove rotifers and other invasive pests from the liquid source material, (IV) a low inoculation concentration algae storage container for storage of at least a portion of the final separation solid-containing fraction, (V) a dryer to dry the final concentrated solid-containing fraction to remove the remaining water to yield a dry target organism (i.e., microalgae) product, or (VI) any combination of (I)-(V). In one embodiment, the algae cell bioactivity or bioavailability is substantially maintained or preserved using the apparatus and method of using same. In another embodiment, the algae cell bioactivity or bioavailability is substantially maintained or preserved only after passage through the separation unit of the apparatus. The details of the apparatuses are described in more detail hereinbelow.

Figure 2:
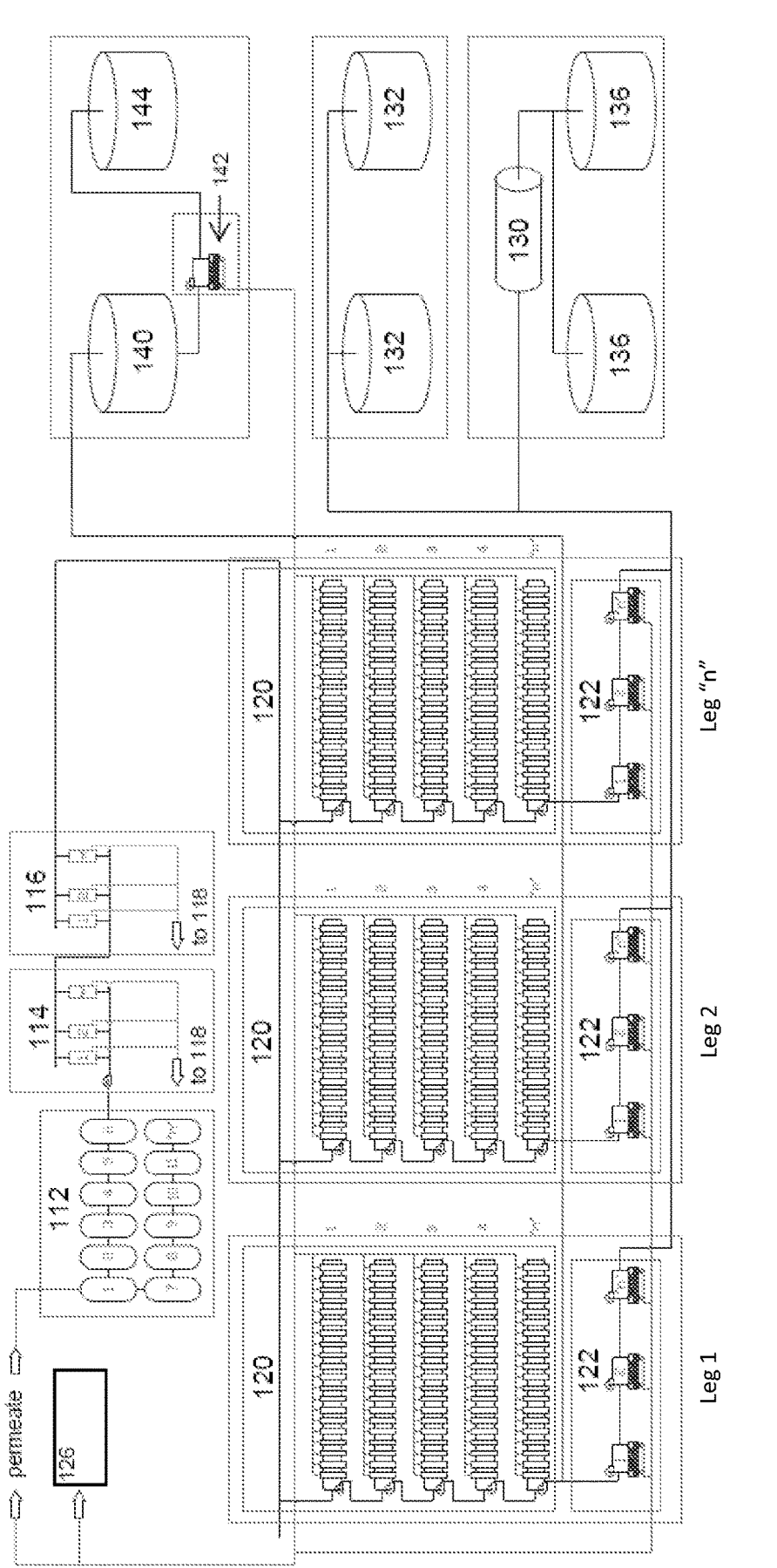
FIG. 2 illustrates another schematic of the apparatus described herein.

Algae can be separated from a liquid source material comprising same using an apparatus 100 such as that shown in FIG. 1 or 2. In FIG. 1, a liquid source material comprising algae can be contained in at least one algae cultivator such as a raceway or other bioreactor 112 including, but not limited to, Photobio Reactors (PBR) or Open Raceway Ponds (ORP), or both. The number of algae cultivators can be one or more than one, e.g., 2-100 or more. When there is more than one algae cultivator, each one can be communicatively connected such that liquid and/or algae pass from one algae cultivator to another in series or each algae cultivator can be set up in parallel thereby isolating each algae cultivator from the others, as readily determined by the skilled artisan. The concentration of algae in the liquid source material prior to any separation is typically in a range from about 0.02 wt % to about 5-6 wt %, depending on the cultivation raceway or bioreactor (i.e., ORP or PBR).

When it is determined that the maximum concentration of algae has been reached in the incubator (e.g., raceway or other bioreactor) 112, the liquid source material can optionally be introduced to at least one pre-filtration unit 114, which removes any unwanted larger materials present in the liquid source material prior to further processing, thus guarding the filters downstream. Because algae is often cultivated in open-air systems, many unwanted materials such as insects, birds, animals, pollen, rocks, tree detritus, and weed detritus are found in the liquid source material. Pre-filtration systems include, but are not limited to, centrifuges, vibrating screens, mesh screening, belt filters, screw presses, hydrocyclones, HELLAN strainers, paddle strainers, sieve bend screens, and other systems that can remove unwanted material to ensure a less hindered flow of the liquid source material through the at least one dewatering/separation apparatus and at least one concentration apparatus. It should be appreciated that the apparatus can comprise one or more pre-filtration units, for example, one, two, three, up to "n" pre-filtration units, as shown in FIG. 2, arranged in series, in parallel, or a combination of both. When there is more than one pre-filtration unit, a pre-filtration unit may be the same as, or different from, other pre-filtration units in the apparatus, with the intent of separating different unwanted materials, having different sizes, more efficiently, as readily understood by the person skilled in the art. The unwanted materials obtained during pre-filtration can be disposed of, harvested for other purposes, or moved to an evaporation pond 118 followed by disposal.

Another optional addition to the apparatus is an invasive pest filtration unit 116. Invasive pests such as rotifers are often present in the liquid source material and may not be removed using other pre-filtration apparatuses. Many invasive pests are larger than the algae and it is beneficial to remove them prior to dewatering/separation. The invasive pests can be removed using any filtration means that can preferentially remove invasive pests, relative to the microalgae, from a liquid source material, pre-filtered or not, as understood by the skilled artisan. It should be appreciated that the apparatus can comprise one or more invasive pest filtration units, for example, one, two, three, up to "n" invasive pest filtration units, as shown in FIG. 2, arranged in series, in parallel, or a combination of both. When there is more than one invasive pest filtration unit, an invasive pest filtration unit may be the same as, or different from, other invasive pest filtration units in the apparatus, with the intent of removing invasive pests more efficiently, as readily understood by the person skilled in the art. The invasive pests obtained during invasive pest filtration can be moved to an evaporation pond 118 and ultimately disposed of or alternatively, separated and sold commercially.

The liquid source material, optionally pre-filtered and/or substantially devoid of invasive pests, is moved to the separation unit 120 comprising at least one separation stage, represented for example by 120.1, 120.2, 120.3, 120.4, up to "n" possible stages (e.g., 120.n) in FIGS. 1 and 2, wherein n=anywhere from 1-50. For the purposes of the present disclosure, the at least one separation stage can comprise one separation apparatus such as an inside-out hollow-fiber filtration apparatus. When there is more than one separation stage, the separation apparatus may be the same as, or different from, the separation apparatuses in the other separation stages, as readily understood by the person skilled in the art.

Hollow-fiber filtration apparatuses used in the art have traditionally been "outside-in" hollow fiber filters (HFF), wherein the feed is introduced outside of the hollow fiber lumen and a liquid fraction passes through the membrane walls to the inside of the hollow fiber lumen. A cake of retentate collects on the outside of the hollow fibers, eventually requiring backflushing of the fibers using water, a gas, or a mixture of both, to remove the cake. Disadvantages of the outside-in hollow fiber apparatus include, but are not limited to, a lack of constant or controlled concentration of the retentate and a lower flux performance.

In the present invention, preferably at least one hollow-fiber filtration apparatus used is an "inside-out" hollow fiber apparatus, wherein a feed is introduced to the inside of a hollow fiber membrane lumen and the liquid permeates from inside the hollow fiber membrane lumen to the outside, driven by at least one pump. The solid-containing fraction, in this case comprising algae species, remains inside the fiber and is moved through the hollow fiber, hence it is cross-flow, to the next stage of the separation unit or to the concentration unit, whichever is directly downstream, as will be discussed hereinbelow. The hollow fiber lumens can be substantially linear or spiralized and the cross-section of the lumen can be substantially circular or elliptical or polygonal or irregularly-shaped. The interior diameter of the hollow fiber lumen can be in a range from about 0.5 mm to about 2 mm, preferably in a range from about 0.5 mm to about 1 mm, even more preferably in a range from about 0.8 mm to 0.85 mm. The pore size of the hollow fiber membranes is selected to ensure that the algae substantially remain inside the hollow fiber lumen during filtration, as readily determined by the person skilled in the art. Advantageously, inside-out HFF apparatuses allow the user to control the shear, yielding a more predictable concentration of the solid-containing fraction.

Users can also select HFF apparatuses having different length hollow fibers. For example, in one embodiment, the initial separation stages can comprise HFF apparatuses having longer fibers. When the concentration of the retentate starts to increase, e.g., in the later separation stages, the pressure drop becomes too large when using the HFF apparatuses with longer fibers and so it becomes advantageous to use a HFF apparatus having fibers that are shorter. Accordingly, in one embodiment, the separation unit comprises at least one HFF apparatus having longer fibers and at least one HFF apparatus having shorter fibers, wherein the shorter fiber HFF apparatus is positioned downstream of the longer fiber HFF apparatus. In another embodiment, each HFF apparatus in the separation unit comprises hollow fibers having the same length. In still another embodiment, the length of the hollow fibers in the second HFF apparatus is shorter than those in the first HFF apparatus, the length of the hollow fibers in the third HFF apparatus is shorter than those in the second HFF apparatus, and so on.

In one embodiment, the separation unit comprises only one separation stage. In another embodiment, the separation unit comprises two, three, four, five, or more ("n") separation stages arranged in series, in parallel, or some combination of both. In some embodiments, the separation stages operate continuously. When operating in series, the solid-containing fraction is serially moved through to a next separation stage in the series, eventually yielding the final separation solid-containing fraction. When operating in parallel, the solid-containing fractions of all of the parallel-arranged separation stages are combined to yield the final separation solid-containing fraction. The liquid fraction (shown as "p" in FIG. 1) from each separation stage is also combined or otherwise leaves the separation unit as described below. It should be appreciated that although it is preferred that each separation stage includes an inside-out hollow fiber apparatus, at least one different separation apparatus may be used as well. In some embodiments, the separation unit comprises 4-6 separation stages, preferably five separation stages, wherein each separation stage uses an inside-out hollow fiber apparatus. In some embodiments, the separation unit comprises more than one separation stage, wherein each separation stage optimizes the flux decay curve, meaning that the first stage performs the most dewatering and thereafter the concentration of the algae as it passes from stage to stage is in small, incremental steps such that the flux rate represents an asymptotic curve, thereby increasing the overall efficiency of the separation unit, and wherein the flux rate in a first separation stage relative to a second separation stage is greater, and so on as the number of separation stages increases to "n." In some embodiments, the separation unit does not comprise any dead-end outside-in hollow fiber separation stages. In some embodiments, the temperatures in the separation unit are in a range from about room temperature to no more than 40° C.

Following passage through the separation unit, the final separation solid-containing fraction (i.e., the cumulative solid-containing fraction that emerges following passage through each of the separation stages) has an algae concentration of about 4 wt % to about 12 wt %, preferably about 8 wt % to about 12 wt %, based on the total weight of the final separation solid-containing fraction. In one embodiment, a substantial amount of the microalgae cells in the final separation solid-containing fraction remain viable. In another embodiment, the optimal separation unit conditions can be altered for industrial processing efficiency depending on the operational goals, which may result in algal cells that are non-viable in the final separation solid-containing fraction.

The final separation solid-containing fraction is then moved out of the separation unit 120 (i) to the concentration unit 122 and/or (ii) to the low inoculation concentration algae storage container 140 (to be discussed further hereinbelow). The first liquid fraction from the separation unit leaves the separation unit and can be recycled by directing (i) back to the at least one algae incubator 112, and/or (ii) to an optional storage container 126 for other uses including, but not limited to, clean-in-place (CIP) flushing of the stages, e.g., separation stages and/or concentration stages, and/or the recovery of metabolites, phytonutrients, minerals and nutrients using nanofiltration and/or reverse osmosis, as readily determined by the skilled artisan. Advantageously, the liquid fraction from the separation unit contains valuable solubilized nutrients that, once returned to the at least one algae incubator 112, can offset the amount of new nutrients that need to be added for new algae growth. Although advantageous to recycle, in some embodiments, it should be appreciated that some or all of the first liquid fraction is discarded.

It should be appreciated by the person skilled in the art that although the at least one separation stage is described as preferentially an inside-out hollow fiber apparatus, other apparatuses can be used instead so long as the overall result is dewatering of the liquid source material to the preferred algae concentration. Other separation apparatuses include, but are not limited to, spiral filters with corrugated spacer, ceramic tangential flow filters, and traditional cassette tangential flow filters, but do not comprise any dead-end outside-in hollow fiber separation stages.

The final separation solid-containing fraction moved to the concentration unit 122 will undergo concentration therein. The concentration unit comprises at least one concentration stage represented for example by 122.1, 122.2, up to "n" possible stages (e.g., 122.n) in FIGS. 1 and 2, wherein n=1-50. For the purposes of the present disclosure, the at least one concentration stage can comprise a concentration apparatus such as a cross-flow filtration cassette, for example, as manufactured by Smartflow Technologies, Inc., Sanford, NC, USA and variously described in the following United States patents: U.S. Pat. Nos. 4,867,876; 4,882,050; 5,034,124; 5,034,124; 5,049,268; 5,232,589; 5,342,517; 5,593,580; 5,868,930; 10,987,631, 11,654,397, and U.S. patent application Ser. No. 18/315,711 filed on May 11, 2023 in the name of Todd Benson, et al., and entitled "Filter Cassette Article, and Filter Comprising Same"; the disclosures of all of which are hereby incorporated herein by reference in their respective entireties. An embodiment of a cross-flow filtration cassette is further described hereinbelow.

When there is more than one concentration stage, each concentration stage comprises a concentration device that is the same as, or different from, concentration devices in the other concentration stages. In some embodiments, the at least one concentration stage can further include a centrifuge, an evaporator, and/or a filter press, as will be discussed below.

In one embodiment, the concentration unit comprises only one concentration stage. In another embodiment, the concentration unit comprises two, three, or more ("n") concentration stages arranged in series, in parallel, or some combination of both. In some embodiments, the concentration units operate continuously. When operating in series, the solid-containing fraction is serially moved through to a next concentration stage in the series, eventually yielding a final concentration solid-containing fraction. When operating in parallel, the solid-containing fractions of all of the parallel-arranged concentration stages are combined to yield the final concentration solid-containing fraction. The liquid fraction (shown as "p" in FIG. 1) from each concentration stage is also combined or otherwise leaves the concentration unit as described below. It should be appreciated that although it is preferred that each concentration stage includes a cross-flow filtration cassette, at least one different concentration apparatus may be incorporated as well, for example at least one centrifuge, at least one evaporator, and/or at least one filter press, as understood by the person skilled in the art. In a preferred embodiment, the concentration unit comprises 2-4 concentration stages, preferably three concentration stages, wherein each concentration stage comprises a cross-flow filtration cassette. In some embodiments, the concentration unit does not comprise any dead-end outside-in hollow fiber concentration stages.

Following passage through the concentration unit, the final concentrated solid-containing fraction (i.e., the solid-containing material that emerges following passage through each of the concentration stages), has an algae concentration of at least 6-8 wt %, or at least 10 wt %, or at least 15 wt %, or at least 20 wt %, or at least 25 wt %, or at least 30 wt %, based on the total weight of the final concentrated solid-containing fraction. The final concentrated solid-containing fraction is then moved out of the concentration unit 122 (i) to a dryer 130 (to be discussed further below) and/or (ii) to a wet concentrated product storage container 132. All of the second liquid fraction from the concentration unit leaves the concentration unit and is recycled by directing (i) to the at least one algae incubator 112, and/or (ii) to an optional storage container 126 for other uses, as readily determined by the skilled artisan. Advantageously, the liquid fraction from the concentration unit contains valuable solubilized nutrients that, once returned to the at least one algae incubator 112, can offset the amount of new nutrients that need to be added for new algae growth. Although advantageous to recycle, in some embodiments, it should be appreciated that some or all of the second liquid fraction is discarded.

An advantage associated with the use of the cross-flow filtration cassettes described herein is that they can be used at higher temperatures than is typically thought possible in the cross-flow filtration arts. The temperature of the final separation solid-containing fraction entering the concentration stages can be in be a range from about 1° C. to about 130° C. For example, if the intent is to maintain the viability of the algae cells in the final separation solid-containing fraction, the temperatures can be maintained below 60° C., for example, in a range from about 1° C. to about 60° C. If the viability of the algae cells is no longer relevant, it is actually beneficial to increase the temperature of the final separation solid-containing fraction because of the increased flux rate associated with moving warmer fluid through the cross-flow filtration cassettes. In the higher temperature situations, ranges contemplated include about 50° C. to about 130° C., about 50° C. to about 85° C., greater than 60° C. to about 130° C., and greater than 60° C. to about 95° C. In a particularly preferred embodiment, the temperature of filtration is in a range from about 50° C. to about 85° C., which can lead to algal cell fractionation which will aid in downstream processing, e.g., lipid extraction. Another advantage associated with the higher temperature concentration unit is that the final concentrated solid-containing fraction entering a dryer is the offset of energy required to dry the final concentrated solid-containing fraction, making the drying process more efficient.

It should be appreciated by the person skilled in the art that although the at least one concentration stage is described as preferentially comprising a cross-flow filtration cassette, other apparatuses can be used instead, or in addition to, so long as the overall result is concentration of the final separation solid-containing fraction to the preferred algae concentration following concentration. For example, the concentration unit can comprise at least one centrifuge and/or at least one evaporating apparatus and/or at least one filter press (not shown). It should also be appreciated by the person skilled in the art that depending on the microalgae target product, there is a concentration crossover point whereby it becomes less expensive to send to the drying unit than to run through another concentration stage.

As introduced, the final concentrated solid-containing fraction emerging from the concentration unit 122 can be sent to at least one dryer 130 to dry the final concentrated solid-containing fraction substantially to dryness. The advantages of an apparatus that comprises both the separation unit and the concentration unit in series (as depicted by the larger dashed box in FIG. 1) include, but are not limited to, the removal of more water from the liquid source material than any of the apparatuses of the prior art, thereby sending a final concentrated solid-containing fraction comprising less water to the dryer and concomitantly lowering the operational cost of drying the microalgae. The lower operational cost can come in the form of a smaller dryer for the same amount of dry algae, or more dry algae obtained from a standard-sized dryer, or the utilization of a lower temperature for drying allowing for improved product quality (e.g., less product loss due to volatility, decreased lipid oxidation potential, increased protein availability, improved processing downstream such as protein concentration and lipid extraction). Dryers that can be used include, but are not limited to, steam drum surface knife dryers, spray dryers, rotary dryers, microwave dryers, tunnel dryers, ring dryers, and any combination thereof. In another alternative, the dryer has low or no heat. Once dry, the dried algae can be stored in container 136. In one embodiment, a dryer is used in the apparatus, for example, non-exogeneous drying. In one embodiment, the dryer uses a pressure differential to "squeeze" the water out of the final concentrated solid-containing fraction (and the algae cells), with or without increasing the surface area of the final concentrated solid-containing fraction (for example by introducing recycled dry material or spraying/aerosolizing). In another embodiment, the dryer utilizes evaporative flash cooling. Regardless of the dryer used, in a preferred embodiment, the product (i.e., the microalgae) is dried indirectly, wherein the product remains at a temperature below about 85° C., more preferably below about 82° C., even more preferably below about 70° C., and most preferably below about 50° C., even though at least a portion of the dryer itself has a much higher temperature. Examples of indirect dryers include, but are not limited to, non-contact heaters or convection dryers. This is possible due to an evaporative cooling effect around the product that is giving up the moisture to the air. There are advantages to drying the final concentrated solid-containing fraction using a pressure change. For example, a large pressure change can lyse the algae cell, which helps with subsequent oil extraction efficiency. In other embodiments, it is preferred that the algae cell wall remain intact so as to minimize the oxidation of the cell thus requiring a more gentle drying approach.

As introduced hereinabove, the final separation solid-containing fraction can also be moved to a low inoculation concentration algae storage container 140. There, the final separation solid-containing fraction can remain in the storage container 140 or can optionally be sent to a concentrator 142 such as a cross-flow filtration cassette, as described herein, to remove additional water. The retentate from the concentrator 142 can be stored in the high inoculation concentration algae storage container 144. Advantageously, the storage of the low and high inoculation concentration algae provides a source of algae seed for the algae incubators. For example, if a production facility is upset by weather, flood, act of god, pest stress (infection), etc., there is traditionally no immediate means to gain back production. Keeping the cells viable in a concentrated state (e.g., the storage containers 140 and 144) allows for the reintroduction (innoculation) of a large concentration of live algae cells to the incubator(s) 112, ensuring that the exponential growth phase is achieved more quickly and the loss of potential harvest minimized.

Advantageously, the apparatus can have multiple "legs" operating simultaneously so that if one leg were offline, for example, for cleaning, the other legs can maintain the continuous processing of the liquid source material to separate the target algae therefrom. For example, referring to FIG. 2, a leg comprises one separation unit, comprising five separation stages (but could be more or less stages), and one concentration unit, comprising three concentration stages (but could be more or less stages), wherein each leg is arranged in parallel to the other legs. The apparatus of FIG. 2 comprises Leg 1, Leg 2, wherein the separation unit 120 and the concentration unit 122 can comprise up to "n" stages, wherein the number of legs "n" can be from 1-100, and wherein the legs are all arranged in parallel, as readily determined by the person skilled in the art.

The advantages of the apparatus described herein are plentiful including, but not limited to:

Algae cultivation usually requires the input of macro/ micro nutrients, such as N, P, Fe, Mg, and others, for the optimal growth in the growth medium. Because the apparatus can recycle the liquid fractions from the separation unit(s) and/or the concentration unit(s) to the at least one algae incubator 112, less nutrient replacement is required in the algae incubator(s), thereby lowering the production costs. In addition, because of the optional invasive pest filtration, pests can be easily removed from the liquid source material, thereby reducing pest stress in the algae incubator(s). Further, because the apparatus is able to concentrate the microalgae without substantially breaking up the algal cells, substantially no cell fragments, which negatively affect algae growth, are not returned to the at least one algae cultivator;

Throughout the harvest and separation process, cell viability can be maintained. This retention is important for a few reasons. First, maintaining the viability of the algae cells in a concentrated state allows for the reintroduction (innoculation) of the concentrated, viable algae cells to the cultivator(s) should the algae cell populations in the cultivator(s) be disrupted, ensuring that the exponential growth phase is achieved more quickly by increasing the speed to repopulation of the cultivation method. For example, if all but a single acre of the viable production of algae cells in a 100 acre pond farm is lost, it would take multiple weeks to return to full production capacity, assuming zero harvests, and hence a loss of three months of production. If you have concentrated viable cells, you can seed the cultivator(s) and move to exponential growth more quickly. Moreover, because the final separation solid-containing fraction comprises less moisture, relative to the apparatuses and methods of the prior art, the amount of storage volume needed for the concentrated inoculation algae cells (in 140 and 144) is lower. Secondly, the ability to maintain cell viability at concentration (in 140 and 144) allows for the more cost effective control and optimization of the algae's environment (e.g., relative to the algae at the cultivation concentration) and hence the algae's physiological characteristics;

Traditionally, chemical aids such as flocculants/coagulants have been used to bind the algae to create a larger particle size for easier separation using Dissolved Air Floatation Technology (DAF) or a centrifuge. There are several constraints to using flocculation including, but not limited to: the operational cost of the chemical (especially if the algae is being used in a human application because a food grade flocculant is required, which increases the cost); the presence of the residual chemical in a closed loop media cultivation system, which can affect the algae growth and production efficiency therein; and the presence of the floc/coagulant in the final dried product. Accordingly, in one embodiment, the apparatus and method described herein does not use flocculation or coagulation (i.e., and as such the apparatus and method described herein is substantially devoid of flocculants and/or coagulants) to separate the microalgae from the liquid source material. In another embodiment, the apparatus and method described herein does not use non-human grade flocculants or coagulants to separate the microalgae from the liquid source material;

Centrifugation has also traditionally been used for the separation and concentration of microalgae. Disadvantages associated with centrifugation include, but are not limited to, the neutral buoyancy and overall density of some microalgae resulting in separation efficiency problems or the breaking of the algae cells due to the sheer force of a centrifuge resulting in fragmented pieces in the liquid fraction (i.e., the supernate), and the creation of cultivation problems or increased invasive species in the cultivation method. In addition, industrial centrifuges have a separation efficiency of only about 70-95% and the high end of the separation efficiency is only achieved with reduced flow rates and high-speed separations. One of the advantages of the present apparatus is the return of the liquid fraction to the at least one cultivator 112, wherein the liquid fraction is substantially free of the target substances originally present in the liquid source materials. Preferably, fragmented algal cells are not returned to the cultivator. Accordingly, in a preferred embodiment, the apparatus and method described herein does not use centrifugation to separate the microalgae from the liquid source material. That said, if commercially more efficient, it is contemplated that at least one centrifuge can be incorporated into the apparatus described herein;

Evaporators have also been traditionally used in the prior art to concentrate microalgae. That said, when evaporation processes are used, many of the nutrients from the liquid source material will remain in the solid-containing fraction and as such must be subsequently separated from the microalgae, which requires additional processing and hence additional costs. Further, as discussed at length herein, one of the advantages of the present apparatus and method of using same is that the liquid fraction is recycled to the at least one cultivator for reuse as cultivation media. Advantageously, the liquid fraction comprises nutrients that can be repeatedly reused, thus minimizing the amount of newly sourced nutrients necessary for the growth of new microalgae in the cultivation media. Any time evaporation is utilized, there is no liquid fraction.

Dead-end filtration, for example outside-in hollow fiber filtration, cannot be used in continuous, steady state, operations but would require a redundant system or fractional system for continuous operation at a minimum increasing capital expenditure. Accordingly, in a preferred embodiment, the apparatus and method described herein does not use dead-end filtration (e.g., outside-in hollow fiber filtration) to separate the microalgae from the liquid source material. In another embodiment, the apparatus and method described herein does not use dead-end filtration in either the separation unit or the concentration unit, but it could be used elsewhere in the apparatus and method;

The cross-flow filtration cassettes used in the apparatus can be rated to run at higher temperatures, for example above about 60° C. to about 95° C., which allows for the final separation solid-containing fraction to pass through at a higher flux;

Overall, the advantage of the apparatus including the dryers described herein is the ability to maintain viability of the algal cells, preserving the quality and quantity of the lipid (contained in said algal cells) and other target substances that would otherwise be at least partially denatured by heat and shear. The dryers described herein preserve bioavailability of the lipids, proteins and carbohydrates of the algae cells, which has not previously been achieved using apparatuses and methods of the prior art.

The apparatus described herein is generally described as comprising at least one incubator, optionally at least one pre-filtration unit, optionally at least one invasive pest filtration unit, at least one leg comprising a separation unit and a concentration unit, and optionally at least one dryer. This reflects the convenience of having the cultivator(s), optional pre-filtered unit(s), leg(s), and optional dryer(s) in one location, especially since many microalgae farms are remotely located and transportation of large volumes of liquids or solids is financially impractical. That said, it should be appreciated by the person skilled in the art that the microalgae can be cultivated offsite and the liquid source material transported to an apparatus comprising optionally at least one pre-filtration unit, optionally at least one invasive pest filtration unit, at least one leg comprising a separation unit and a concentration unit, and optionally at least one dryer. In other words, the liquid source material can be pre-filtered prior to transport to an apparatus comprising at least one leg comprising a separation unit and a concentration unit. In should also be appreciated that the viable final separation solid-containing fraction can be transported off-site to other inoculation storage containers for seeding other incubators. Moreover, it should be appreciated that the final concentrated solid-containing fraction can be transported offsite for drying and/or storage and/or for seeding other incubators. Other arrangements are easily envisioned by the person skilled in the art.

Microalgae

In one embodiment, the cultivated algae comprises at least one species selected from the group consisting of freshwater algae such as *Chlorella vulgaris, Spirullina* sp., or *Cryptomonas ovate*; brackish species like *Nannochlorpsis australis, Nannochlorpsis gaditara, Nannochloropsis granulate, Nannochloropsis limnetica, Nannochloropsis oceanica, Nannochloropsis oculate, Nannochloropsis salina*, and other *Nannochloropsis* sp.; marine species such as *Skeletonema costatum, Chaetoceros gracilis* marine diatoms, *Tetraselmis* sp., *Isochyrsis galbana*, or *Rhodomonas minuta*, or hypersaline species like *Dunaliella salina*. In one embodiment, the cultivated algae comprises substantially one single species in order to obtain a specific lipid profile or other targeted value-added compositional ingredient. In another embodiment, combinations of algae species are cultivated in the same series of ponds, to create an algal product with a particular lipid profile or other targeted value-added compositional ingredient not otherwise obtainable from a single algal species. It should be appreciated that combinations of algae can either be cultivated together from the outset, or grown in parallel then mixed, in order to create a population of algae having the preferred lipid profile. The algae can be cultivated photoautotrophically or heterotrophically. In a preferred embodiment, the cultivated algae comprises, consists of, or consists essentially of *Nannochloropsis*.

While this harvest and concentration technology can be used on most any microalgae, the information disclosed herein is specific to the operational parameters associated with the cultivation, harvesting and separation of the microalgae *Nannochloropsis* from a liquid growth medium. The person skilled in the art would be fully capable of using the information disclosed herein to adapt the apparatus and method as necessary if the obtainment of a different microalgae is preferred.

Figure 5:
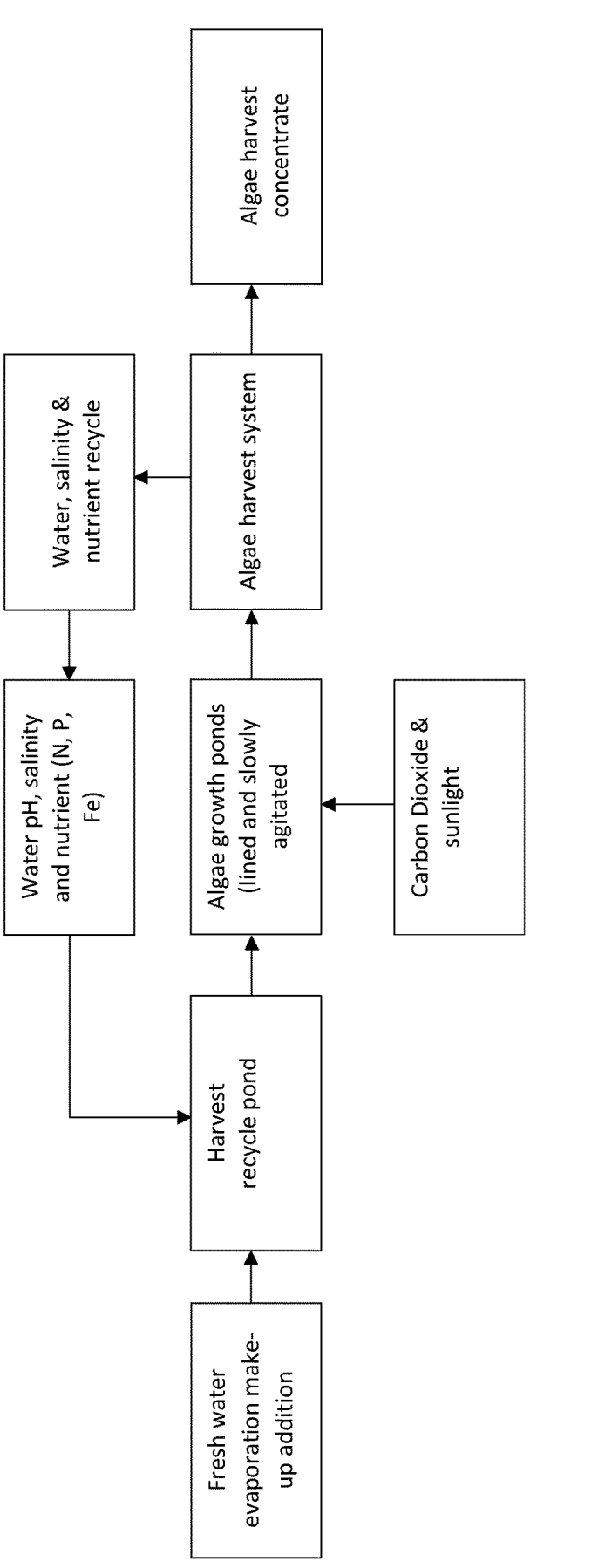
FIG. 5 illustrates a high-level process flow diagram of the growth process.

*Nannochloropsis* is typically commercially grown in the open ponds requiring slightly brackish water for growth. Salt can be added to raise the salinity to the appropriate range for *Nannochloropsis*. The water is also supplemented with the addition of nitrogen (N), phosphorus (P), and iron (Fe) (in the form of a fertilizer) as vital nutrients to ensure optimal algal growth. Additional micronutrients that are not found in the water supply are supplied as required by algal growth optimization analysis but are also approved feed ingredients. Water salinity level is preferably checked onsite daily, and N and P levels checked weekly, at a minimum. A high-level process flow diagram of the growth process is provided in FIG. 5, wherein the "Algae Harvest Concentrate" is the material collected using the apparatus and method described herein.

Cross-Flow Filtration Cassettes

Figure 3:
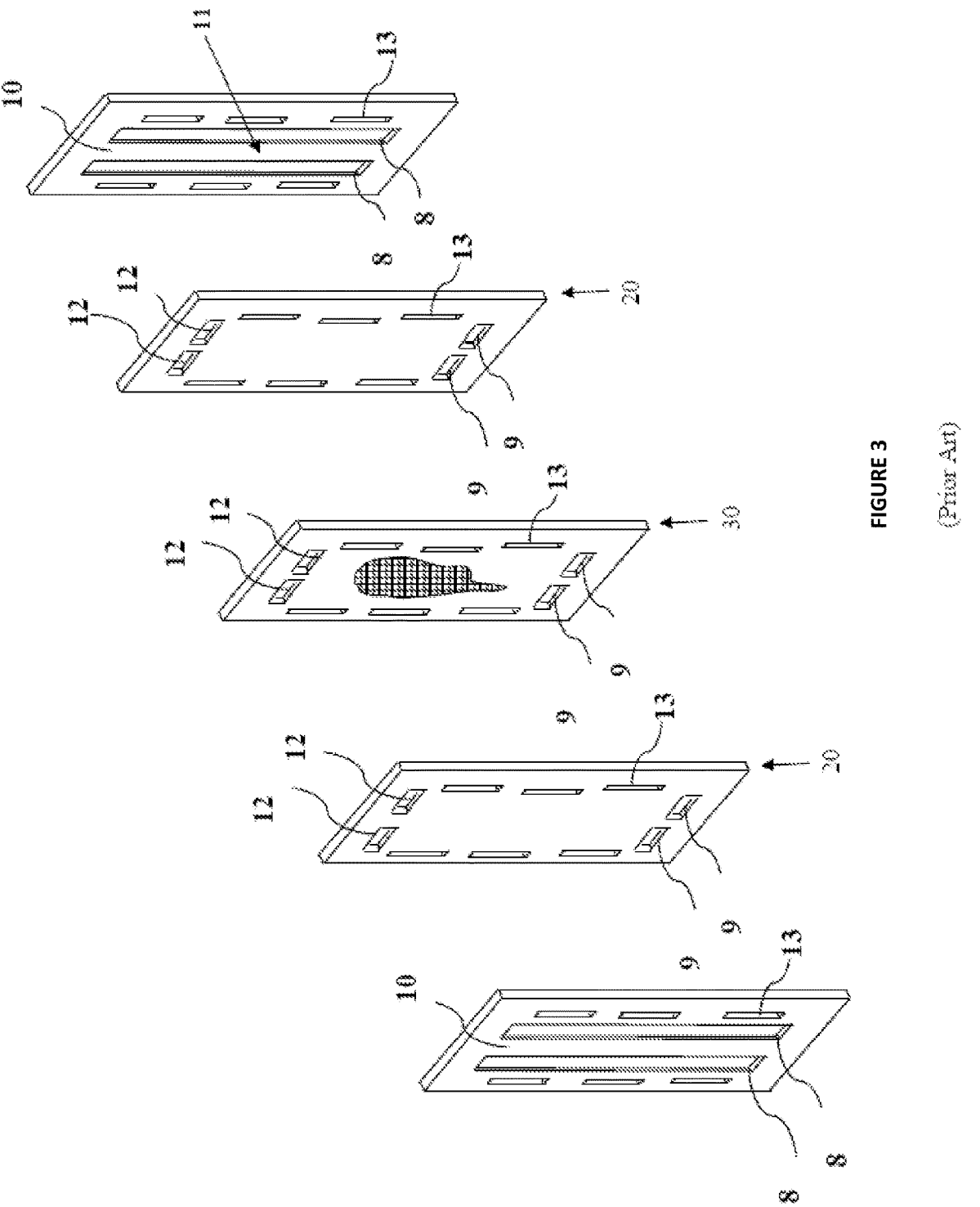
FIG. 3 is a perspective view of the assembly of sheets in a cross-flow filtration cassette of the prior art, wherein the assembly end plates are not shown.

Briefly, a generalized embodiment of a preferred cross-flow filtration cassette is shown in FIG. 3, said filtration cassette comprising at least one assembly, wherein the at least one assembly comprises a multilaminate array of sheet members of generally rectangular and generally planar shape with main top and bottom surfaces and a first end and a second end along the longitudinal axis, wherein the sheet members include in sequence in said array a first assembly end plate (not shown), a first retentate sheet (10), a first filter sheet (20), a permeate sheet (30), a second filter sheet (20), a second retentate sheet (10), and a second assembly end plate (not shown), wherein each of the assembly end plate, permeate sheet members, and filter sheet members in said array have at least one retentate cutout opening (9) at a first end thereof, and at least one retentate cutout opening (12) at opposite second end thereof, with permeate passage openings (13) at longitudinal side margin portions of the sheet members. Each of the first and second retentate sheets (10) have at least one channel opening (8) therein, extending longitudinally between the first end retentate (9) and second end retentate (12) openings of the permeate and filter sheets in the array. The sheets are bonded (e.g., compression, adhesive, or both) to adjacent sheets about peripheral end and side portions thereof, with their retentate cutout openings and permeate passage openings in register with one another, wherein a central portion of each of the sheets is unbonded to permit liquid source material to flow down the channel opening(s) such that permeate flows through the filter sheet (20) to the permeate sheet (30), and to permit the permeate in the permeate sheet (30) to flow towards the permeate passage openings to the permeate outlet. For ease of disclosure, the first end retentate (9) and second end retentate openings (12) (and permeate passage openings (13)) are illustrated in FIG. 3 as generally rectangular or square but can be an irregular pentagon. It should be appreciated by the person skilled in the art that the shape of the retentate openings (and permeate passage openings) are not limited to rectangles or squares or irregular pentagons and can include any other reasonable shape for the flow of fluid therethrough, as readily understood by the person skilled in the art. Two assembly end plates sandwich the multilaminate array of sheets, wherein the two assembly end plates comprise at least one fluid opening at the first end thereof, and at least one fluid opening at the second end thereof, or both, in register with the fluid openings of the array. In addition, the at least one assembly can further comprise at least one of options (I), (II), (III), or (IV), or any combination of (I)-(IV): (I) a cap positioned on at least a portion of the first end fluid opening(s) or at least a portion of the second end fluid opening(s), or both, of a permeate pack, wherein the permeate pack comprises the first filter sheet, the permeate sheet, and the second filter sheet members, wherein the cap is positioned proximate to the channel openings of the first and second retentate sheets; (II) the fluid openings at the first end, the fluid openings at the second end, or both the fluid openings at the first and second end, are cut as an irregular pentagon having a "V" positioned proximate to the channel openings of the first and second retentate sheets; (III) a first permeate screen spacer positioned between the first filter sheet and the permeate sheet, a second permeate screen spacer positioned between the second filter sheet and the permeate sheet, or both, wherein each permeate screen spacer has a first end and a second end corresponding to that of the multilaminate array of sheets, wherein the permeate screen spacers comprise at least one fluid opening at the first end thereof and at least one fluid opening at the second end thereof, wherein fluid openings of the permeate screen spacers are in register with corresponding fluid openings of the permeate pack; (IV) the permeate sheet comprises a metal matrix or other reinforced porous material of requisite thickness. In some embodiments, the cap cap has a general U-shape and transverses the permeate pack through the fluid opening and at least partially overlaps a first side of the first filter sheet and at least partially overlaps a second side of the second filter sheet, with the permeate sheet positioned therebetween. In some embodiments, with regards to option (IV), a width of the permeate passage opening of the permeate sheet is less than a width of the permeate passage opening of each of the filter sheets and retentate sheets in the multilaminate array of sheets.

Figure 4:
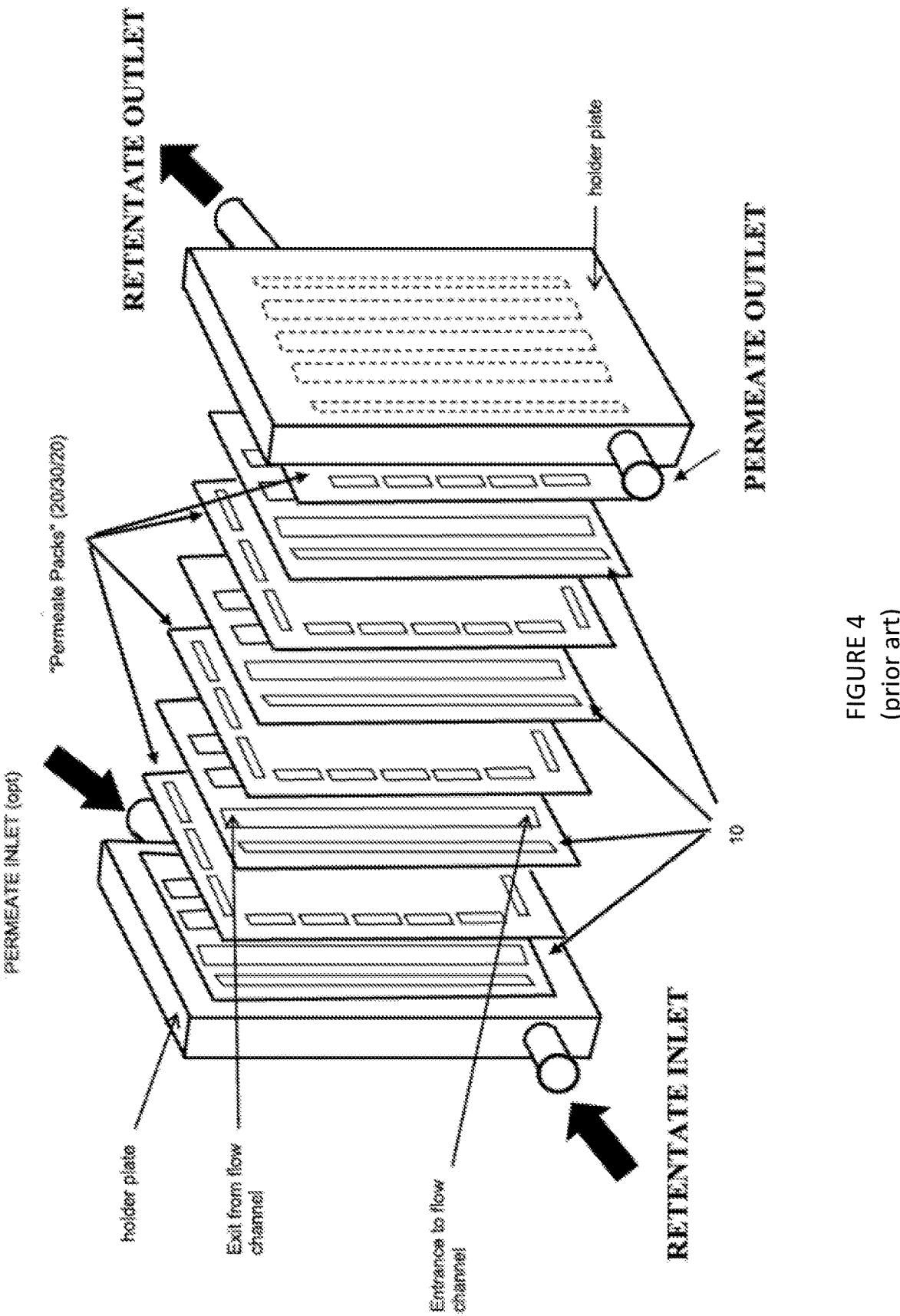
FIG. 4 illustrates the flow pattern of the fluid through an assembly of sheets between holder plates with transversely located first end fluid and second end fluid openings, a permeate outlet, and an optional permeate inlet.

The cross-flow filtration cassettes are mounted between holder plates, which may be provided with suitable ports, for introduction of liquid source material to be separated in the cassettes, and for discharge or withdrawal of filtrate/permeate and retentate (see, e.g., FIG. 4). One skilled in the art can appreciate that the assembly end plates can be integrally sealed to the assembly of sheets to have a single module comprised of assembly end plates and at least one assembly of sheets. If the integrally sealed assembly end plates are of plastic or polymeric materials or sheets, the units may provide the function of a disposable device for single or multiple use.

In the use of cross-flow filtration cassettes, the specificity and speed of a desired separation is effected by a number of factors including, but not limited to, a) fluid distribution in the cross-flow module, b) channel height of the cross-flow module, c) channel length, d) shear rate, e) sheet pore structure, f) sheet structure, g) sheet chemistry, h) transmembrane pressure, i) osmotic force, j) hydrophobic/hydrophilic differential, k) liquid source material modification, l) temperature, and m) pressure drop, which is a function of applied pressure channel length, velocity and solution viscosity.

For use in the present apparatus and method, the pore size of the filter sheets are selected to ensure that the specific algae and other targeted material do not pass through the filter sheets during filtration, i.e., do not pass through the filter sheet and enter the permeate stream, as readily determined by the person skilled in the art.

It is well known in the art that there can be benefits to working with a higher temperature fluid because the viscosity of the fluid can decrease as the temperature increases. As a result, the permeate flux passage is improved with a concomitant decrease in the energy expenditure and processing costs. Further, smaller capacity pumps can be used and heat exchangers and buffer tanks can be eliminated. Another advantage is the ability to achieve a higher percentage solids target at a higher temperature relative to that achieved at the lower temperatures of the prior art. Towards that end, the assembly end plates, the filter sheets, the retentate sheets, and permeate sheets (and the optional permeate screen spacer sheets) are made of materials which are adapted to accommodate high temperatures, so that the interior surfaces of the filtration cassette are able to withstand higher processing temperature and/or extreme pH and may be steam sterilized and/or chemically sanitized solutions for regeneration and reuse, as "steam-in-place" and/or "sterilizable in situ" structures, respectively. In one embodiment, liquid source materials having temperatures in a range from about 1° C. to about 130° C. can be introduced into the cross-flow filter cassettes. Other temperature ranges contemplated include about 50° C. to about 130° C., about 50° C. to about 85° C., greater than 60° C. to about 130° C., and greater than 60° C. to about 95° C. Alternatively, the entire cassette may be formed of materials which render the cassette disposable in character.

Method of Use

In a second aspect, a method of separating a target organism, e.g., microalgae, from a liquid source material using the apparatus described herein is disclosed, wherein said method comprises introducing a liquid source material to the apparatus eventually yielding a final concentrated solid-containing fraction comprising the target organism.

In one embodiment, a method of obtaining microalgae from a liquid source material is disclosed, wherein the microalgae have a concentration in a final concentrated solid-containing fraction of at least 6-8 wt %, or at least 10 wt %, or at least 15 wt %, or at least 20 wt %, or at least 25 wt %, or at least 30 wt %, based on the total weight of the final concentrated solid-containing fraction, wherein the method comprises introducing a liquid source material to an apparatus described herein to yield the final concentrated solid-containing fraction. The advantages of the method described herein are numerous and to the inventors' knowledge, have never been achieved before using the apparatuses and methods of the prior art.

In one embodiment of the second aspect, a method of obtaining microalgae from a liquid source material is described, wherein the microalgae have a concentration in a final concentrated solid-containing fraction of at least 6-8 wt %, or at least 10 wt %, or at least 15 wt %, or at least 20 wt %, or at least 25 wt %, or at least 30 wt %, based on the total weight of the final concentrated solid-containing fraction, wherein the method comprises:

introducing a liquid source material to an apparatus to yield the final concentrated solid-containing fraction, said apparatus comprising:

at least one leg for separating and concentrating a liquid source material to yield the final concentrated solid-containing fraction, wherein each leg comprises:

(i) a separation unit comprising at least one separation stage, wherein each separation stage comprises an apparatus that can dewater the liquid source material to yield a first liquid fraction and a separation stage solid-containing fraction, wherein when there is more than one separation stage, they are communicatively connected (I) in series, and a separation stage solid-containing fraction is serially moved through to a next separation stage in the series for additional dewatering, or (II) in parallel, wherein separation stage solid-containing fractions from each separation stage are combined, or (III) some combination of both (I) and (II), eventually yielding a final separation solid-containing fraction; and (ii) a concentration unit comprising at least one concentration stage, wherein each concentration stage comprises an apparatus that can concentrate the final separation solid-containing fraction to yield a second liquid fraction and a concentrated solid-containing fraction, wherein when there is more than one concentration stage, they are communicatively connected (I) in series, and a concentration stage solid-containing fraction is serially moved through to a next concentration stage in the series for additional concentration, or (II) in parallel, wherein concentration stage solid-containing fractions from each concentration stage are combined, or (III) some combination of both (I) and (II), eventually yielding the final concentrated solid-containing fraction.

In some embodiments, prior to passage through the apparatus, the concentration of microalgae in the liquid source material is less than about 4 wt %, based on the total weight of the liquid source material.

In another embodiment of the second aspect, a method of obtaining microalgae from a liquid source material is described, wherein prior to the method, the concentration of microalgae in the liquid source material is greater than about 4 wt %, based on the total weight of the liquid source material, and wherein subsequent to the method the microalgae have a concentration in a final concentrated solid-containing fraction of at least 6-8 wt %, or at least 10 wt %, or at least 15 wt %, or at least 20 wt %, or at least 25 wt %, or at least 30 wt %, based on the total weight of the final concentrated solid-containing fraction, wherein the method comprises:

introducing a liquid source material to an apparatus to yield the final concentrated solid-containing fraction, said apparatus comprising:

at least one leg for concentrating a liquid source material to yield the final concentrated solid-containing fraction, wherein each leg comprises a concentration unit comprising at least one concentration stage, wherein each concentration stage comprises an apparatus that can concentrate the final separation solid-containing fraction to yield a second liquid fraction and a concentrated solid-containing fraction, wherein when there is more than one concentration stage, they are communicatively connected (I) in series, and a concentration stage solid-containing fraction is serially moved through to a next concentration stage in the series for additional concentration, or (II) in parallel, wherein concentration stage solid-containing fraction from each concentration stage are combined, or (III) some combination of both (I) and (II), eventually yielding the final concentrated solid-containing fraction.

The apparatus of the embodiments of the second aspect can further comprise at least one of (I) at least one incubator upstream of at least one leg, where the microalgae are cultivated, (II) at least one pre-filtration unit to remove unwanted materials from a liquid source material comprising the cultivated microalgae to yield a pre-filtered liquid source material, (III) at least one invasive pest filtration unit to remove rotifers and other invasive pests from the liquid source material, (IV) a low inoculation concentration algae storage container for storage of at least a portion of the final separation solid-containing fraction, (V) a dryer to dry the final concentrated solid-containing fraction to remove the remaining water to yield a dry target organism (i.e., microalgae) product, or (VI) any combination of (I)-(V). In one embodiment, the algae cell bioactivity or bioavailability is substantially maintained or preserved using the apparatus. In another embodiment, the algae cell bioactivity or bioavailability is substantially maintained or preserved only after passage through the separation unit of the apparatus. The method of the embodiments of the second aspect can further comprise at least one of (I) harvesting the microalgae present in at least one incubator to obtain the liquid source material comprising the microalgae, (II) pre-filtering the liquid source material to remove unwanted materials therefrom to yield a pre-filtered liquid source material, (III) filtering of the liquid source material or the pre-filtered liquid source material to remove rotifers and other invasive pests, (IV) storing at least a portion of the final separation solid-containing fraction in a low inoculation concentration algae storage container, (V) drying the final concentrated solid-containing fraction to remove the remaining water to yield a dry microalgae product, or (VI) any combination of (I)-(V).

Advantageously, relative to the methods of the prior art, the method described herein is capable of removing more water from the liquid source material comprising microalgae cells (i.e., concentrating the microalgae cells more). This has multiple advantages including, but not limited to, requiring less storage capacity for an equivalent dry matter content, reducing the cost of drying the final concentrated solid-containing fraction because less water is present, and permitting the use of alternative drying methods, e.g., non-exogenous drying and the other drying methods described herein.

That which is claimed is:

1. A method of obtaining microalgae from a liquid source material, wherein the microalgae have a concentration in a final concentrated solid-containing fraction of at least 10 wt %, based on the total weight of the final concentrated solid-containing fraction, wherein the method comprises:

introducing a liquid source material to an apparatus to yield the final concentrated solid-containing fraction, said apparatus comprising:

at least one leg for separating and concentrating a liquid source material to yield the final concentrated solid-containing fraction, wherein each leg comprises:

(i) a separation unit comprising at least one separation stage, wherein each separation stage comprises an apparatus that can dewater the liquid source material to yield a first liquid fraction and a separation stage solid-containing fraction, wherein when there is more than one separation stage, they are communicatively connected (I) in series, and a separation stage solid-containing fraction is serially moved through to a next separation stage in the series for additional dewatering, or (II) in parallel, wherein separation stage solid-containing fractions from each separation stage are combined, or (III) combination of both (I) and (II), eventually yielding a final separation solid-containing fraction; and (ii) a concentration unit comprising at least one concentration stage, wherein each concentration stage comprises an apparatus that can concentrate the final separation solid-containing fraction to yield a second liquid fraction and a concentrated solid-containing fraction, wherein when there is more than one concentration stage, they are communicatively connected (I) in series, and a concentration stage solid-containing fraction is serially moved through to a next concentration stage in the series for additional concentration, or (II) in parallel, wherein concentration stage solid-containing fractions from each concentration stage are combined, or (III) combination of both (I) and (II), eventually yielding the final concentrated solid-containing fraction.

2. The method of claim 1, further comprising drying the final concentrated solid-containing fraction.

3. The method of claim 1, wherein prior to introduction to the apparatus, the liquid source material is introduced to at least one pre-filtration unit to remove unwanted materials from the liquid source material, wherein the at least one pre-filtration unit comprises a device selected from the group consisting of centrifuges, vibrating screens, mesh screening, belt filters, screw presses, hydrocyclones, HEL-LAN strainers, paddle strainers, and sieve bend screens.

4. The method of claim 1, wherein prior to introduction to the apparatus, the liquid source material is introduced to at least one invasive pest filtration unit to remove invasive pests from the liquid source material.

5. The method of claim 1, wherein the separation unit comprises from one to 50 separation stages.

6. The method of claim 1, wherein at least one separation stage comprises an inside-out hollow fiber filtration apparatus, wherein a feed is introduced inside of a hollow fiber lumen and a liquid fraction permeates from inside the hollow fiber lumen to outside of the hollow fiber lumen.

7. The method of claim 1, wherein a plot of flux rate in each separation unit as a function of dry matter content resembles an asymptotic curve.

8. The method of claim 1, wherein the concentration unit comprises from one to 50 concentration stages, wherein each concentration stage comprises a concentration device that is the same as, or different from, concentration devices in the other concentration stages.

9. The method of claim 8, wherein the concentration device is selected from the group consisting of a cross-flow filtration cassette, a centrifuge, an evaporator, and a filter press.

10. The method of claim 9, wherein the cross-flow filtration cassette comprises at least one assembly, wherein the at least one assembly comprises:

a multilaminate array of sheet members of generally rectangular and generally planar shape, each sheet of the array having a first end, a second end longitudinally opposite the first end, and a thickness, wherein the sheet members comprise in sequence in said array, a first retentate sheet, (a permeate pack and a second retentate sheet) n, wherein n=1, 2, 3, 4, 5, 6, 7, 8, 9, 10, or more, wherein the permeate pack comprises a first filter sheet, a permeate sheet, and a second filter sheet, wherein each sheet in each permeate pack has at least one fluid opening at the first end thereof and at least one fluid opening at the second end thereof, wherein corresponding fluid openings at the first end of each sheet in each permeate pack are in register with one another and corresponding fluid openings at the second end of each sheet in each permeate pack are in register with one another, wherein the first and second retentate sheets have at least one channel opening therein, each channel opening extending longitudinally between a first channel entrance positioned proximate to fluid openings at the first end of the permeate pack and a second channel entrance positioned proximate to fluid openings at the second end of the permeate pack in the array, and wherein the at least one channel opening is open through the entire thickness of the first and second retentate sheets to permit a fluid to contact adjacent filter sheets, and wherein the first and second retentate sheets are bonded to adjacent filter sheets about peripheral end and side portions thereof; and two assembly end plates sandwiching the multilaminate array of sheets, each end plate having a first end and a second end corresponding to that of the multilaminate array of sheets, wherein the two assembly end plates comprise at least one fluid opening at the first end thereof and at least one fluid opening at the second end thereof, wherein fluid openings of the end plates are in register with corresponding fluid openings of the permeate pack, wherein the at least one assembly further comprises at least one permeate passage opening at longitudinal side margin portions of the assembly.

11. The method of claim 10, wherein the cross-flow filtration cassette further comprises at least one of options (I), (II), (III), or (IV), or any combination of (I)-(IV):

(I) a cap positioned on at least a portion of at least one fluid opening of the permeate pack, wherein the cap is positioned proximate to channel entrances of the first and second retentate sheets;

(II) the fluid openings at the first end, the fluid openings at the second end, or both the fluid openings at the first and second end, are cut as an irregular pentagon having a "V" positioned proximate to the channel openings of the first and second retentate sheets;

(III) a first permeate screen spacer positioned between the first filter sheet and the permeate sheet, a second permeate screen spacer positioned between the second filter sheet and the permeate sheet, or both, wherein each permeate screen spacer has a first end and a second end corresponding to that of the multilaminate array of sheets, wherein the permeate screen spacers comprise at least one fluid opening at the first end thereof and at least one fluid opening at the second end thereof, wherein fluid openings of the permeate screen spacers are in register with corresponding fluid openings of the permeate pack;

(IV) the permeate sheet comprises a metal matrix or other reinforced porous material of requisite thickness.

12. The method of claim 1, wherein prior to introduction to the at least one leg, the microalgae are cultivated in at least one incubator.

13. The method of claim 12, wherein the at least one incubator comprises a Photobio Reactor (PBR) and/or an Open Raceway Pond (ORP).

14. The method of claim 1, wherein a portion of the final separation solid-containing fraction is directed to a low inoculation concentration algae storage container.

15. The method of claim 1, wherein at least 50% of the microalgae cells in the final separation solid-containing fraction are viable.

16. The method of claim 1, further comprising recycling the first liquid fraction, the second liquid fraction, or both, back to at least one incubator for reuse as cultivation media.

* * * * *